(12) United States Patent
Cheng et al.

(10) Patent No.: US 9,549,786 B2
(45) Date of Patent: Jan. 24, 2017

(54) METHOD OF MANUFACTURING SURGICAL TEMPLATE POSITIONING DEVICE

(71) Applicant: TAIWAN IMPLANT TECHNOLOGY COMPANY, Kaohsiung (TW)

(72) Inventors: Ying lung Cheng, Kaohsiung (TW); Hsiao ching Wang, Kaohsiung (TW); Yi nung Ho, Kaohsiung (TW)

(73) Assignee: TAIWAN IMPLANT TECHNOLOGY COMPANY, Kaohsiung (TW)

( * ) Notice: Subject to any disclaimer, the term of this patent is extended or adjusted under 35 U.S.C. 154(b) by 145 days.

(21) Appl. No.: 14/569,710

(22) Filed: Dec. 14, 2014

(65) Prior Publication Data

US 2015/0099241 A1 Apr. 9, 2015

Related U.S. Application Data

(63) Continuation-in-part of application No. 13/904,044, filed on May 29, 2013, now abandoned.

(30) Foreign Application Priority Data

Aug. 23, 2012 (TW) .............................. 101216286 U

(51) Int. Cl.
*A61C 3/00* (2006.01)
*A61C 1/08* (2006.01)
*A61B 6/14* (2006.01)

(52) U.S. Cl.
CPC *A61C 1/084* (2013.01); *A61B 6/14* (2013.01)

(58) Field of Classification Search
CPC .................................. A61C 1/084; A61B 6/14
See application file for complete search history.

(56) References Cited

U.S. PATENT DOCUMENTS

| | | | | |
|---|---|---|---|---|
| 5,967,777 | A * | 10/1999 | Klein | A61C 1/084 433/75 |
| 2009/0042167 | A1* | 2/2009 | Van Der Zel | A61C 1/084 433/215 |
| 2011/0045431 | A1* | 2/2011 | Groscurth | A61C 1/084 433/74 |
| 2012/0053593 | A1* | 3/2012 | Abboud | A61C 1/084 606/96 |

* cited by examiner

*Primary Examiner* — Robert N Wieland
(74) *Attorney, Agent, or Firm* — Mark M. Friedman

(57) ABSTRACT

A surgical template positioning device is provided, and has a template and a dental mold. The template has a first surface formed with at least three spherical recesses, a second surface, and a guiding hole. The dental mold has at least three spherical portions partially embedded in the at least three spherical recesses and an implanted hole having an axis the same as the guiding hole. The at least three spherical recesses have three spherical centers as being three vertices of a triangle, the axis passes through the triangle, and the at least three spherical portions have spherical centers corresponding with the three vertices of the triangle. A method of manufacturing the surgical positioning device is also provided.

10 Claims, 6 Drawing Sheets

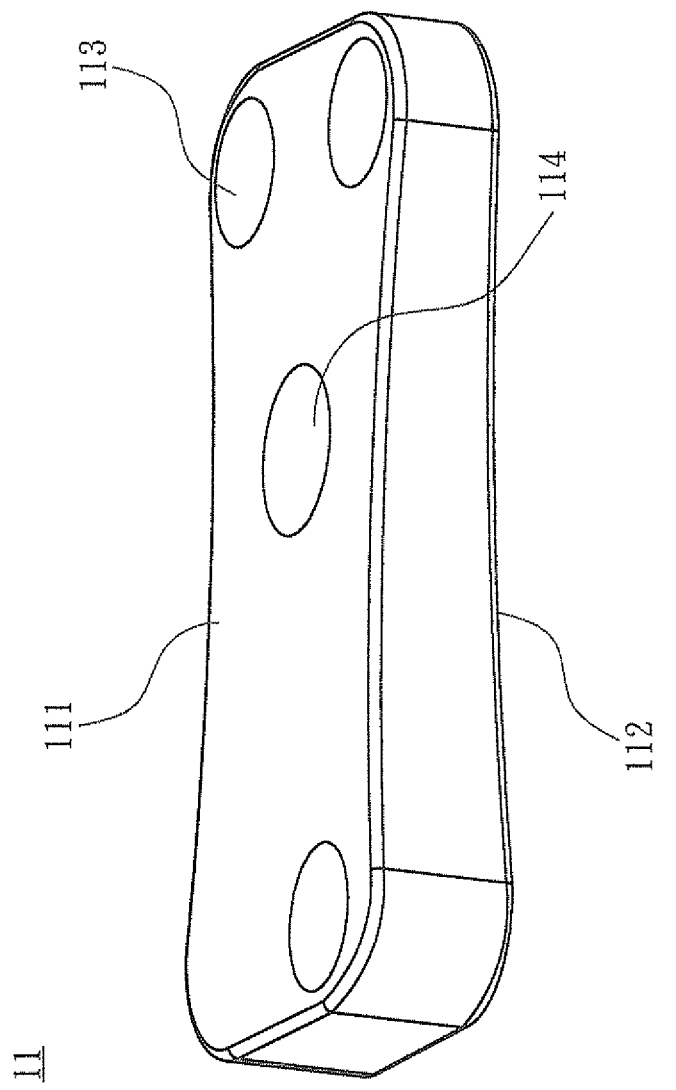

METHOD OF MANUFACTURING SURGICAL TEMPLATE POSITIONING DEVICE

CROSS REFERENCE TO RELATED APPLICATIONS

This application is a continuation-in-part application of U.S. patent application Ser. No. 13/904,044, filed on May 29, 2013, now abandoned, the disclosure of which is incorporated herein by reference.

FIELD OF THE INVENTION

The present invention relates to an artificial implant field, and more particularly to a method of manufacturing of a surgical template positioning device having spherical recesses and spherical portions.

BACKGROUND OF THE INVENTION

The tooth implant is a prosthetic tooth for substituting a whole tooth or a partial true tooth, and thus can solve the disadvantages that the traditional movable prosthetic tooth is not stably firmed or the bone matrix shrinks after many years. In the conventional implantation treatment, when the dentist performs an implant drilling surgery, the tooth implant is firstly designed based on a tooth computed tomography (CT) machine. Parameters during constructing a 3D model by scanning images can be collected to decide an ideal location, angle and depth of implanting, so as to correspondingly manufacture a surgical template positioning device.

However, even though the tooth computed tomography (CT) machine can provide an effective surgical simulated environment, such as effectively displaying the height and thickness of the alveolar bone and the actual distribution locations of nerves and blood vessels and exchanging different viewing angles for surveying the predefined position of tooth implant, it is still limited by the outline of the conventional positioning pins. When the positioning pins are not parallel to each other, the actual relative position will not be able to accurately labeled and thereby causing a parameter reading error, so as to manufacture a defective template. Once such a template is acquired, it is difficult for the dentist to further correct the template based on the actual situation of the oral cavity of the patient.

Because pre-operative assessment defect causes the deviation and dislocation of the drilling position, depth and angle, an artificial tooth implant can not be disposed on a pre-set position, and thus unnecessary complications and medical malpractice occurs.

As a result, it is necessary to provide a method of manufacturing a surgical template positioning device to solve the problems existing in the conventional technologies, as described above.

SUMMARY OF THE INVENTION

A primary object of the present invention is to provide a surgical template positioning device and a method of manufacturing the same, which uses three non-collinear points to determine a plane, so as to actually represent the oral cavity of the patient and reduce an inevitable deviation. Under the premise of controlling the coordination and symmetry of function and appearance, after reconstructing, it can achieve an expected ideal target.

A secondary object of the present invention is to provide a surgical template positioning device and a method of manufacturing the same, which does not require an extra puncture orientation to the gums of the patient, so as to reduce the discomfort in the surgical process and also save the manufacturing time and the cost of the surgical template positioning device. The surgical template positioning device can even be cooperated with a size-fixed sleeve to decrease the steps of replacing the template, so as to shorten the time in surgery.

To achieve the above objects, the present invention provides a surgical template positioning device which comprises:

a template having a first surface formed with at least three spherical recesses, a second surface opposite to the first surface, and a guiding hole passing through the template; and a dental mold having at least three spherical portions partially embedded in the at least three spherical recesses and an implanted hole having an axis and coaxially aligned with the guiding hole;

wherein the at least three spherical recesses have three spherical centers as being three vertices of a triangle, the axis passes through the triangle, and the at least three spherical portions have spherical centers corresponding with the three vertices of the triangle.

In one embodiment of the present invention, the shape of the spherical recesses is complementary to the shape of the spherical portions.

In one embodiment of the present invention, the depth of the spherical portions is greater than a scanning span of a tooth computed tomography (CT) machine.

In one embodiment of the present invention, the guiding hole is tilted with respect to the first surface of the template, and the guiding hole is vertical with respect to the second surface of the template.

In one embodiment of the present invention, the diameter of the guiding hole is greater than or equal to an outer diameter of a drill sleeve, and the diameter of the implanted hole is greater than or equal to the diameter of the guiding hole.

In one embodiment of the present invention, the template further comprises at least one water-introducing hole disposed close to and communicated with the guiding hole.

To achieve the above object, the present invention further provides a method of manufacturing a surgical template positioning device, comprising steps of:

preparing a dental mold from a patient, wherein the dental mold has a simulation prosthetic tooth and at least three spherical portions formed on a platform of the dental mold and surrounding the simulation prosthetic tooth, and the at least three spherical portions have spherical centers corresponding with the three vertices of the triangle;

wearing the dental mold on gums of the patient and performing a tooth computed tomography on the dental mold and the alveolar bone of the patient, so as to obtain data of the patient and the dental mold;

providing a template having at least three spherical recesses on a first surface, wherein the spherical centers of the at least three spherical recesses define three vertices of a triangle;

digitally planning an implanted hole for the dental mold and a guiding hole for the template having an axis and coaxially aligned with the implanted hole according to the data of the patient and the dental mold;

forming the guiding hole passing through the template according to the triangle and the axis;

removing the simulation prosthetic tooth from the dental mold;

combining and fixing the template with the dental mold; and forming the implanted hole passing through the dental mold by using the guiding hole of the template.

In one embodiment of the present invention, the simulation prosthetic tooth is made of a first material visible under X-ray irradiation.

In one embodiment of the present invention, the first material of the simulation prosthetic tooth is barium sulfate.

In one embodiment of the present invention, at least the spherical portions are made of a second material visible under X-ray irradiation, which is different from the first material.

In one embodiment of the present invention, the second material of the spherical portions is ceramic or zirconia.

In one embodiment of the present invention, after forming the implanted hole, an implant drill hole is drilled into the alveolar bone of the patient through the guiding hole and the implanted hole by a drill tool for disposing a tooth implant on the alveolar bone, wherein the simulation prosthetic tooth is used as a reference of the tooth implant.

In comparison with the conventional techniques, the present invention improves the poor practicability of the surgical template positioning device. Based on 3D reconstruction through a tooth computed tomography (CT) machine and accompanied with at least three spherical portions which are not collinear on a platform of a dental mold and surrounding the simulation prosthetic tooth, the scanning data are collected and then the parameters of the curvature and radius are calculated to acquire the relative position of each spherical center for actually representing the status of the oral cavity of the patient, so as to manufacture an improved template. After that, the patient wears such a customized template and dental mold on the gums and the alveolar bone, and the dentist conveniently uses the template to perform a tooth implanting surgery, which is used to effectively drill on the edentulous portion of the alveolar bone to insert artificial tooth roots, so as to reduce the fault caused by the preoperative assessment. Therefore, damage to the important nerves, blood vessels, and organs in surgery can be avoided, so as to significantly enhance the safety and the success rate of tooth implanting and also considerably reduce the discomfort of the patient in implanting process.

In regard to the features and implementation of the present invention, preferred embodiments in concert with figures are described in detail hereinafter.

DESCRIPTION OF THE DRAWINGS

FIGS. 3A to 3C are schematic views of the surgical template positioning device according to one embodiment of the present invention;

DETAILED DESCRIPTION OF THE PREFERRED EMBODIMENTS

The structure and the technical means adopted by the present invention to achieve the above and other objects can be best understood by referring to the following detailed description of the preferred embodiments and the accompanying drawings. Furthermore, directional terms described by the present invention, such as upper, lower, front, back, left, right, inner, outer, side, longitudinal/vertical, transverse/horizontal, etc., are only directions by referring to the accompanying drawings, and thus the used directional terms are used to describe and understand the present invention, but the present invention is not limited thereto.

Figure 1:
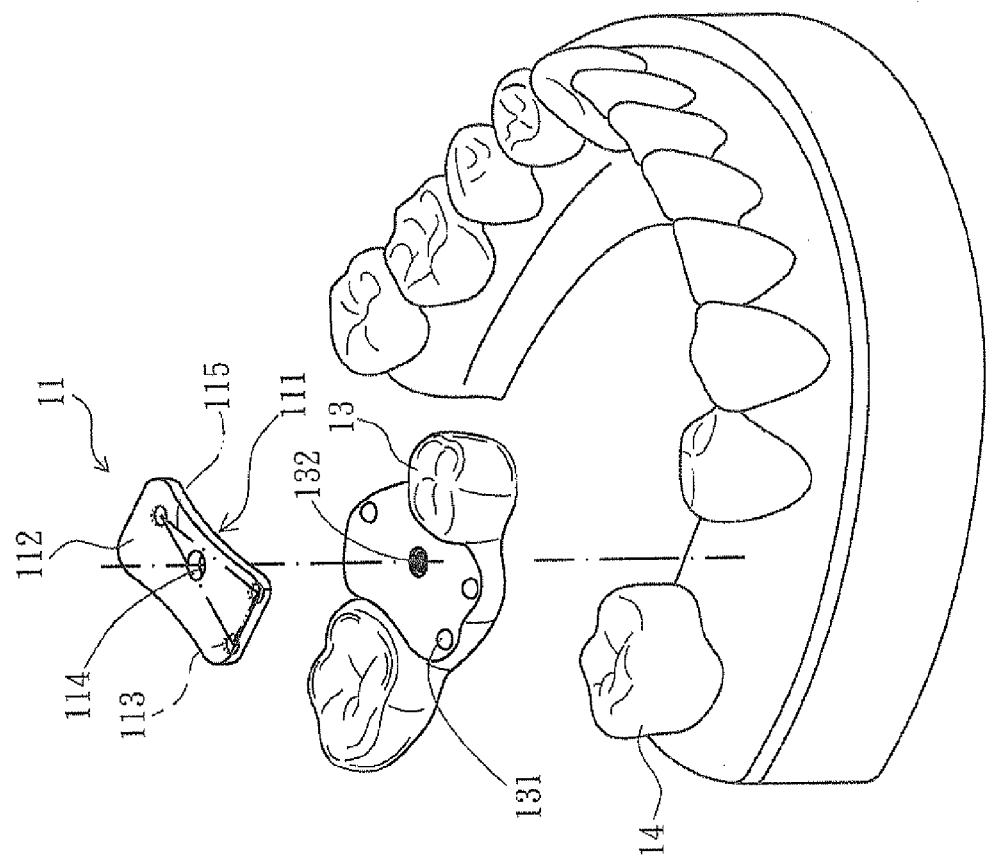
FIG. 1 is a schematic view of a surgical template positioning device according to one embodiment of the present invention.

Referring to FIG. 1, a surgical template positioning device 10 according to one embodiment of the present invention is illustrated, wherein the surgical template positioning device 10 mainly comprises: a template 11, and a dental mold 13. The template 11 has a facing-down first surface 111 (i.e. a lower surface) and a facing-up second surface 112 (i.e. an upper surface) opposite to the first surface 111, wherein the first surface 111 is formed with at least three spherical recesses 113 and a guiding hole 114; relative positions of the spherical recesses 113 commonly define a triangle 115; and the guiding hole 114 passes through the template 11 and formed between the first surface 111 and the second surface 112.

Figure 4:
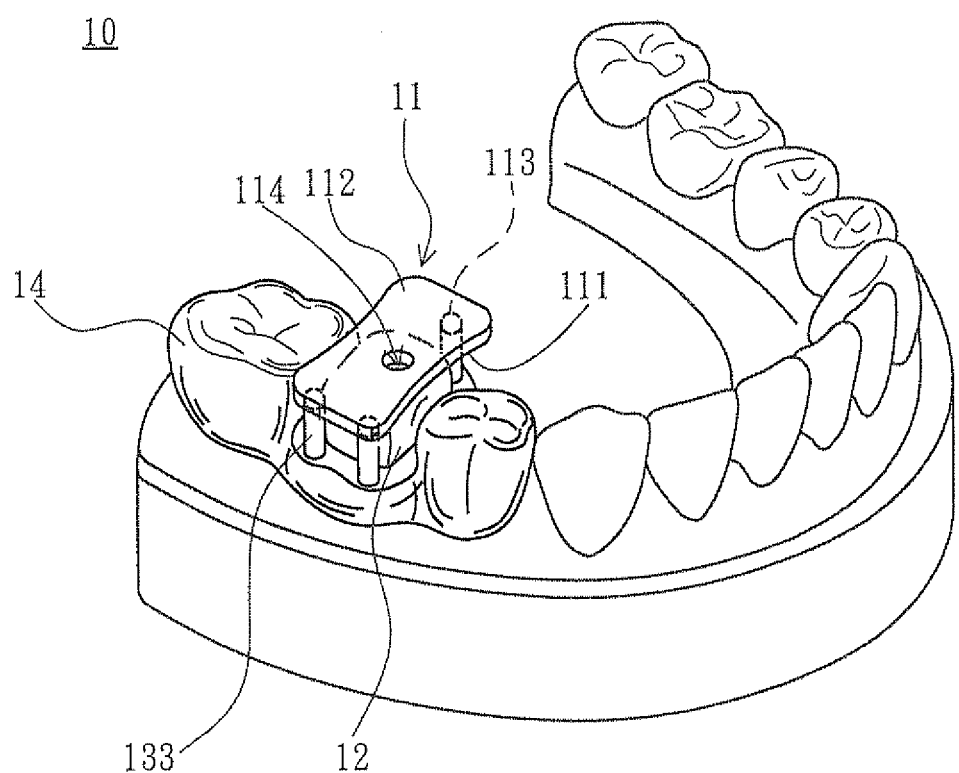
FIG. 4 is a schematic view of the surgical template positioning device according to another embodiment of the present invention.
Figure 5:
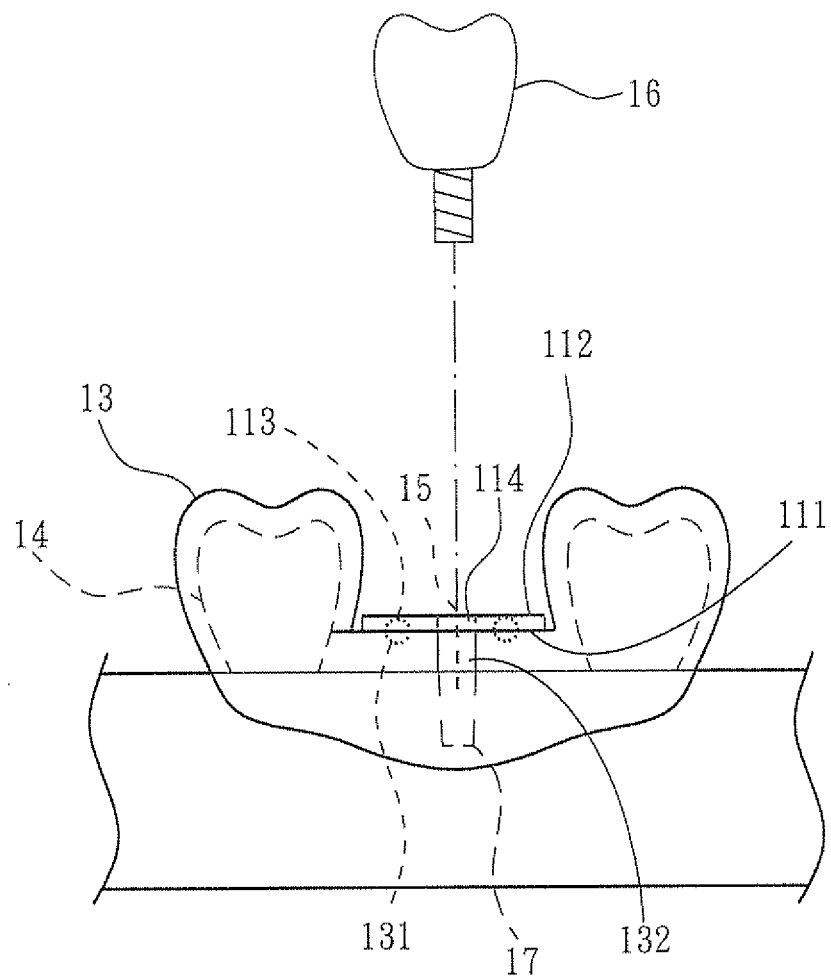
FIG. 5 is a schematic view of a surgical template positioning device and a tooth implant according to one embodiment of the present invention.

The dental mold 13 has at least three spherical portions 131 protruded upward from a platform of the dental mold 13 and one implanted hole 132 passing through the dental mold 13, wherein the spherical portions 131 are combined with the corresponding spherical recesses 113 of the first surface 111, and can surround a simulation prosthetic tooth (i.e. a simulation prosthetic tooth 12 as shown in FIG. 4) when the simulation prosthetic tooth is placed on the platform of the dental mold; and the simulation prosthetic tooth is only used as a reference of a true prosthetic tooth (such as a tooth implant 16 as shown in FIG. 5). The guiding hole 114 corresponds to the implanted hole 132. The implanted hole 132 has an axis 15 the same as that of the guiding hole 114, so that the guiding hole 114 is coaxially aligned with the implanted hole 132. The at least three spherical recesses 113 have three spherical centers used as three vertices of the triangle 115. The axis 15 passes through a virtual plane formed by the triangle 115, and the at least three spherical portions 131 have spherical centers corresponding with the three vertices of the triangle 115.

The present invention will describe the detailed structures, the assembly relationship, and the operative principle of each foregoing element in the preferred embodiments in more detail according to FIGS. 1 to 4 hereinafter.

Figure 2:
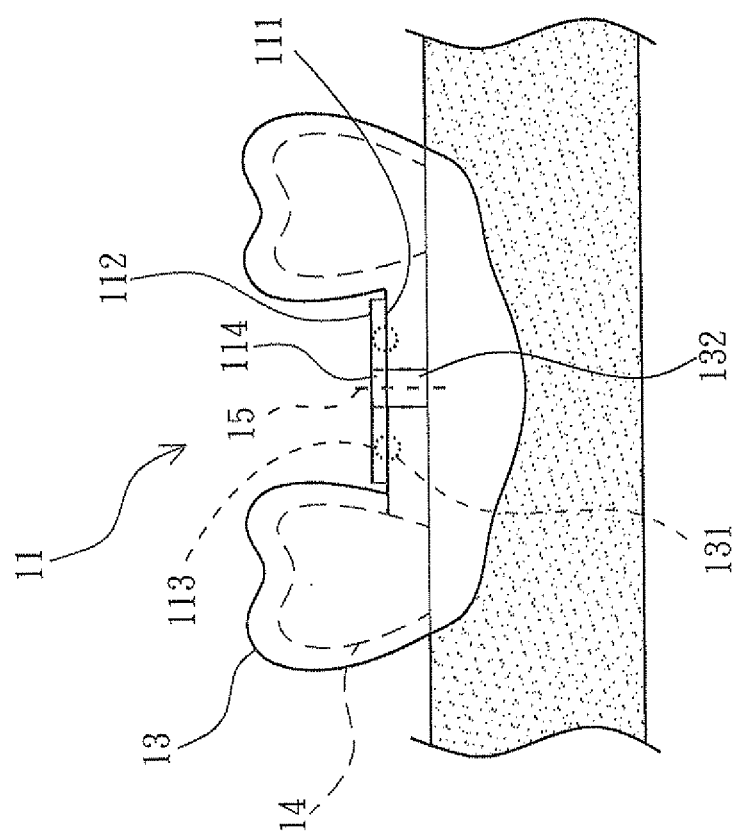
FIG. 2 is a cross-sectional view of the surgical template positioning device according to one embodiment of the present invention.

Referring to FIGS. 1 and 2, a schematic view of a surgical template positioning guide according to one embodiment of the present invention and a cross-sectional view of the surgical template positioning guide according to one embodiment of the present invention are illustrated. In comparison with the conventional cylindrical positioning pin members, the positioning member of the invention, that is, at least three spherical portions 131 formed as hemispherical-like structures and preferably use the materials having a high recognition, such as ceramic or zirconia having a high density feature. According to the high scanning resolution of a tooth computed tomography (CT)

machine or an X-ray machine, 3D dimension of the oral cavity of the patient is virtually presented. The dentist is based on the outline of the spherical portions 131 and relative positions to operate 3D reconstruction. The present invention also can use portions of other shapes, such as elliptic, and the relative positions of the portions is calculated and analyzed by computing. It is worth noted that, the number of the spherical recesses 113 and the spherical portions 131 in the present invention can also be more than three (i.e. four, five, six or more) to certainly present a 3D reconstruction. Moreover, the material of the simulation prosthetic tooth (not-shown) surrounded by the at least three spherical portions 131 can be barium sulfate ($BaSO_4$), so that the simulation prosthetic tooth can also be recognized by the tooth computed tomography (CT) machine or an X-ray machine.

3D reconstruction and the tooth implanting planning are further integrated and converted for molding a plaster mode (not shown) to represent the actual oral shape of the patient, comprising the features of teeth and soft tissues. Next, a thermoplastic resin and self-curing acrylic resin is used to cover the plaster mode to be a fixed shape, the residual portions of the edge are cut off and then a surface dental mold 13 is acquired. In particular, when the patient has a large area of edentulous regions, even complete edentulous, also can operate the surgery by matching the soft tissues with bone nails. The generation of a guiding hole and an implanted hole that the bone nail inserted into is the same as a guiding hole and an implanted hole of the artificial tooth implant, wherein the thermoplastic resin material can be resin, but not limited thereto.

Figure 3B:
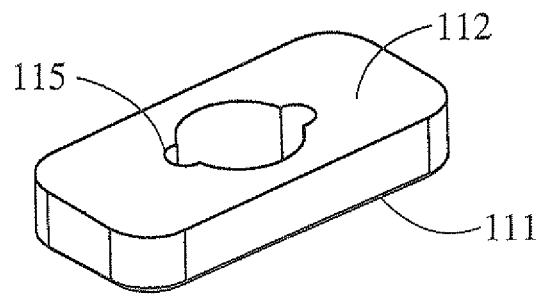

Referring to FIGS. 3A to 3B, schematic views of a first surface 111 of the template 11 according to one embodiment of the present invention are illustrated. The spherical portions 131 are scanned by the tooth computed tomography (CT) machine to acquire a surface curvature, and then the surface curvature and the known radius are calculated to acquire the coordinate of a spherical center. Furthermore, the depth (the radius) of the spherical portions 131 is greater than a scanning span of the tooth CT, such as 2 mm or 3 mm, but it is not limited thereto. After that, the spherical recesses 113 are used to form with three non-collinear reference points; that is, the spherical centers of the spherical recesses 113 commonly determine a plane to form one 3D coordinate through the tooth computed tomography (CT) to produce the customized template 11, wherein the shape of the spherical recesses 113 is complemented to the shape of the spherical portions 131, so that the template 11 can tightly combine with and positioned on the dental mold 13. In the embodiment, the spherical recesses 113 are not limited to hemispherical recesses of 180 degrees, an user also can adjust the degree thereof according to actual situations, such as selecting arc spherical recesses having a degree smaller or greater than 180 degree. Preferably, the template 11 comprises at least one water-introducing hole 115 close to and communicated with the guiding hole 114, as shown in FIG. 3B. The water-introducing hole 115 is used for introducing water to cool down the operation temperature during the implant operation.

Figure 3C:
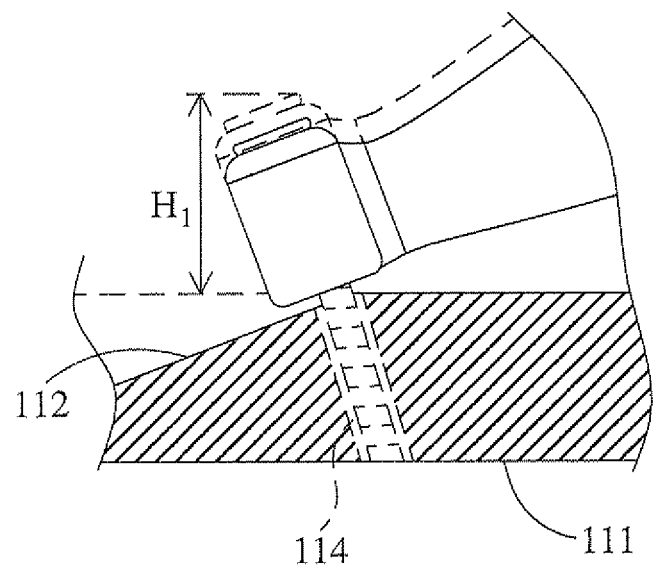

After the template 11 is manufactured through a working machine (not-shown), the template 11 is then placed on the dental mold 13 for drilling the implanted hole 132 into the dental mold 13 by a dental drill (as shown in FIG. 3C), wherein the guiding hole 114 is vertical with respect to the first surface 111 and the second surface 112 of the template 11; or can be tilted with respect to the first surface 111 of the template 11 and vertical with respect to the second surface 112 of the template 11, as shown in FIG. 3C; furthermore, the first surface 111 of the template 11 can be not parallel with respect to the second surface 112.

When the template 11 is placed on the dental mold 13, a dental drill is used to drill at a tilted angle. The second surface 112 (i.e. the upper surface) can be partially removed for reducing the operation height H1. Thus, the guiding hole 114 will be vertical with respect to the second surface 112, but tilted with respect to the first surface 111 (i.e. the lower surface) with a tilted angle. In one embodiment of the present invention, the inner diameter of the guiding hole 114 is greater than or equal to an outer diameter of a drill sleeve, and the inner diameter of the implanted hole 132 is greater than or equal to the inner diameter of the guiding hole 114.

Referring to FIG. 4, a schematic view of a surgical template positioning device according to another embodiment of the present invention is illustrated and similar to the embodiment of FIG. 1, so that the second embodiment uses similar terms or numerals as those of the abovementioned embodiment. As shown, the surgical template positioning device 10 similarly comprises: a template 11 and a dental mold 13. The template 11 has a facing-down first surface 111 and a facing-up second surface 112, wherein the first surface 111 is formed with at least three spherical recesses 113 and a guiding hole 114, relative positions of the spherical recesses 113 commonly define a triangle 115, and the guiding hole 114 passes through the template 11. The dental mold 13 has at least three cylindrical portions 133 and one implanted hole 132, wherein the cylindrical portions 133 preferably use the materials having a high recognition, such as ceramic or zirconia having a high density feature; and each of the top ends of the cylindrical portions 133 have a spherical portion (unlabeled), the spherical portion is correspondingly combined with the spherical recess 113 of the first surface 111, and the guiding hole 114 corresponds to the implanted hole 132. The dental mold 13 helps to temporarily fixe a simulation prosthetic tooth 12 onto a soft tissue between adjacent teeth 14, wherein the simulation prosthetic tooth 12 is used as a reference of a true prosthetic tooth (such as a tooth implant 16 as shown in FIG. 5). It is worth noting that, the number of the spherical recesses 113 and the cylindrical portions 133 of the present invention can also be more than three (i.e. four, five, six or more) to certainly present 3D reconstruction. The simulation prosthetic tooth 12 is also formed by a material visible under X-Ray irradiation, which is different from the material of the cylindrical portions 133, wherein the material of the simulation prosthetic tooth 12 can be barium sulfate ($BaSO_4$), so that the simulation prosthetic tooth 12 can be recognized by a tooth computed tomography (CT) machine or an X-ray machine.

When the alveolar bone of the patient is defective, deformed, or excessively tilted, under the premise of not cutting the gums to fill bone graft powder, the dentist can consider the oral cavity of the patient based on different requirements, so as to adjust at least three cylindrical portions 133 of the dental mold 13. Similarly, for exact positioning, each of the top ends of the cylindrical portions 133 has a spherical portion, so as to be advantageous to effectively drill a defined implanted hole at an actual position of the alveolar bone by a drill tool. The present invention can also use the cylindrical portions 133 having the spherical portions on the top ends thereof to cooperate with the spherical portions 131 of the dental mold 13 for achieving the same object.

Furthermore, a method of manufacturing a surgical template positioning device according to one embodiment of the present invention is also provided, and mainly comprises the following steps of: (S1) preparing a dental mold from a patient; (S2) wearing the dental mold on gums of the patient and performing computed tomography on the dental mold and the alveolar bone of the patient, so as to obtain data of the patient and the dental mold; (S3) providing a template having at least three spherical recesses on a first surface; (S4) digitally planning an implanted hole for the dental mold and a guiding hole for the template according to the data; (S5) forming the guiding hole passing through the template; (S6) removing the simulation prosthetic tooth from the dental mold; (S7) combining the template with the dental mold; and (S8) forming the implanted hole passing through the dental mold by using the guiding hole of the template.

Firstly, the method of manufacturing a surgical template positioning device according to a preferred embodiment of the present invention is the step (S1): preparing a dental mold from a patient, wherein the dental mold has a simulation prosthetic tooth and at least three spherical portions arranged on a platform of the dental mold and surrounding the simulation prosthetic tooth, and the at least three spherical portions have spherical centers corresponding with the three vertices of the triangle. The simulation prosthetic tooth is formed by a material visible under X-Ray irradiation, which is different from the material of the cylindrical portions 133 (i.e. ceramic or zirconia), wherein the material of the simulation prosthetic tooth can be barium sulfate (BaSO$_4$) that is also different from the traditional material of a true prosthetic tooth (such as a tooth implant 16 as shown in FIG. 5), so that the simulation prosthetic tooth can be recognized by a tooth computed tomography (CT) machine or an X-ray machine. Therefore, 3D data of the at least three spherical portions and the simulation prosthetic tooth, such as 3D images and coordinates, can be obtained at the same time.

Next, the method of manufacturing a surgical template positioning device according to a preferred embodiment of the present invention is the step (S2): wearing the dental mold on gums of the patient and performing computed tomography on the dental mold and the alveolar bone of the patient. In this step, the purpose is to obtain data of the patient and the dental mold, especially the height and thickness of the alveolar bone, the actual distribution locations of nerves and blood vessels, and the coordinates of the simulation prosthetic tooth and the at least three spherical portions.

Next, the method of manufacturing a surgical template positioning device according to a preferred embodiment of the present invention is the step (S3): providing a template having at least three spherical recesses on a first surface, wherein the spherical centers of the at least three spherical recesses define three vertices of a triangle. That is to say, the triangle has three vertices corresponding with the spherical centers of the at least three spherical recesses.

Next, the method of manufacturing a surgical template positioning device according to a preferred embodiment of the present invention is the step (S4): digitally planning an implanted hole for the dental mold and a guiding hole for the template having an axis and coaxially aligned with the implanted hole according to the abovementioned data. The simulation prosthetic tooth made of X-ray recognizable material can be used for surface reference, so that the conventional surface scan can be omitted.

Next, the method of manufacturing a surgical template positioning device according to a preferred embodiment of the present invention is the step (S5): forming the guiding hole passing through the template according to the triangle and the axis. The axis passes through the triangle. Based on the same triangle, the guiding hole can be aligned in correspondence with the implanted hole. Preferably, the guiding hole is tilted with respect to the first surface of the template and vertical with respect to a second surface of the template, as shown in FIG. 3C, wherein the first surface 111 of the template 11 is not parallel to the partially removed second surface 112.

Next, the method of manufacturing a surgical template positioning device according to a preferred embodiment of the present invention is the step (S6): removing the simulation prosthetic tooth from the dental mold.

Next, the method of manufacturing a surgical template positioning device according to a preferred embodiment of the present invention is the step (S7): combining the template with the dental mold. The relative position can be referred back to FIG. 5.

Finally, the method of manufacturing a surgical template positioning device according to a preferred embodiment of the present invention is the step (S8): forming the implanted hole passing through the dental mold by guiding a drill tool through using the guiding hole of the template.

After the step (S8), the surgical template positioning device 10 can be used to drill an implant drill hole 17 through the guiding hole 114 and the implanted hole 132 by a drill tool (not-shown) into the alveolar bone of the patient for disposing a tooth implant 16 (i.e. a true prosthetic tooth) with a threaded tooth root on the alveolar bone, as shown in FIG. 5.

As described above, in comparison with the conventional techniques, the present invention improves the poor practicability of the surgical template positioning device. Based on 3D reconstruction through a tooth computed tomography (CT) machine and accompanied with at least three spherical portions 131 which are not collinear on the dental mold 13, the scanning data are collected, and then the parameters of the curvature and radius are calculated to acquire the relative position of each spherical center for actually representing the status of the oral cavity of the patient, so as to manufacture an improved template 11. After that, the patient wears such a customized template 11 and the dental mold 13 on the gums and the alveolar bone, and the dentist conveniently uses the template 11 and the dental mold 13 to perform a tooth implanting surgery, which is used to effectively drill on the edentulous portion of the alveolar bone to insert artificial tooth roots, so as to reduce the fault caused by the preoperative assessment. Therefore, damage to the important nerves, blood vessels, and organs in surgery can be avoided, so as to significantly enhance the safety and the success rate of tooth implanting and also considerably reduce the discomfort of the patient in the implanting process.

The present invention has been described with a preferred embodiment thereof and it is understood that many changes and modifications to the described embodiment can be carried out without departing from the scope and the spirit of the invention that is intended to be limited only by the appended claims.

What is claimed is:

1. A method of manufacturing a surgical template positioning device, comprising steps of:
   preparing a dental mold from a patient, wherein the dental mold has a simulation prosthetic tooth and at least three spherical portions formed on a platform of the dental mold and surrounding the simulation prosthetic tooth;
   wearing the dental mold on gums of the patient and performing a tooth computed tomography on the dental mold and the alveolar bone of the patient, so as to obtain data of the patient and the dental mold;

providing a template having at least three spherical recesses on a first surface, wherein the spherical centers of the at least three spherical recesses define three vertices of a triangle, and the at least three spherical portions have spherical centers corresponding with the three vertices of the triangle;

digitally planning an implanted hole for the dental mold and a guiding hole for the template having an axis and coaxially aligned with the implanted hole according to the data of the patient and the dental mold;

forming the guiding hole passing through the template according to the triangle and the axis;

removing the simulation prosthetic tooth from the dental mold;

combining and fixing the template with the dental mold; and forming the implanted hole passing through the dental mold by using the guiding hole of the template.

2. The method according to claim 1, wherein the shape of the spherical recesses is complementary to the shape of the spherical portions.

3. The method according to claim 1, wherein the depth of the spherical portions is greater than a scanning span of a tooth computed tomography machine.

4. The method according to claim 1, wherein the guiding hole is tilted with respect to the first surface of the template, and the guiding hole is vertical with respect to a second surface of the template opposite to the first surface.

5. The method according to claim 1, wherein the template further comprises at least one water-introducing hole disposed close to and communicated with the guiding hole.

6. The method according to claim 1, wherein the simulation prosthetic tooth is made of a first material visible under X-ray irradiation.

7. The method according to claim 6, wherein the first material of the simulation prosthetic tooth is barium sulfate.

8. The method according to claim 6, wherein the spherical portions are made of a second material visible under X-ray irradiation, which is different from the first material.

9. The method according to claim 8, wherein the second material of the spherical portions is ceramic or zirconia.

10. The method according to claim 1, wherein after forming the implanted hole, an implant drill hole is drilled into the alveolar bone through the guiding hole and the implanted hole by a drill tool of the patient for disposing a tooth implant on the alveolar bone, wherein the simulation prosthetic tooth is used as a reference of the tooth implant.

* * * * *